(12) United States Patent
Bergfjord

(10) Patent No.: US 10,371,232 B2
(45) Date of Patent: Aug. 6, 2019

(54) TORQUE REACTION IN ROTATING MEDICAL APPARATUS

(71) Applicant: Elekta Limited, West Sussex (GB)

(72) Inventor: Per Harald Bergfjord, West Sussex (GB)

(73) Assignee: Elekta Limited, West Sussex (GB)

( * ) Notice: Subject to any disclaimer, the term of this patent is extended or adjusted under 35 U.S.C. 154(b) by 259 days.

(21) Appl. No.: 15/484,336

(22) Filed: Apr. 11, 2017

(65) Prior Publication Data

US 2017/0292587 A1  Oct. 12, 2017

(51) Int. Cl.

| *F16F 15/30* | (2006.01) |
|---|---|
| *A61C 1/18* | (2006.01) |
| *A61B 6/00* | (2006.01) |
| *A61N 5/10* | (2006.01) |
| *H02K 7/02* | (2006.01) |
| *A61B 6/03* | (2006.01) |
| *A61N 5/01* | (2006.01) |

(52) U.S. Cl.
CPC .............. *F16F 15/30* (2013.01); *A61B 6/035* (2013.01); *A61B 6/4435* (2013.01); *A61C 1/186* (2013.01); *A61N 5/01* (2013.01); *A61N 5/1081* (2013.01); *H02K 7/02* (2013.01)

(58) Field of Classification Search
CPC ...... F16F 15/30; A61B 6/4435; A61B 6/4476; A61B 6/035; A61C 1/181; A61C 1/185; A61C 1/186; A61N 5/1081; H02K 7/02; H02K 7/10; H02K 7/00
See application file for complete search history.

(56) References Cited

U.S. PATENT DOCUMENTS 9,358,865 B1 *   6/2016  Sherry ................... B60K 6/105
2010/0020918 A1  1/2010  Popescu et al.

FOREIGN PATENT DOCUMENTS

| BE | 906099 A2 | 4/1987 |
|---|---|---|
| GB | 2018391 A | 10/1979 |
| GB | 2053412 A | 2/1981 |
| JP | S57200744 A | 12/1982 |
| JP | H02107844 A | 4/1990 |

* cited by examiner

*Primary Examiner* — Don K Wong
(74) *Attorney, Agent, or Firm* — Finnegan, Henderson, Farabow, Garrett & Dunner, L.L.P.

(57) ABSTRACT

A system and method for compensating for torque reaction forces in a medical apparatus is disclosed. The system may include a rotary element which rotates about an axis. A contra-rotating flywheel may be driven to rotate about the axis relative to the rotary element, wherein the flywheel is free to rotate and is accelerated and decelerated by a driver which is fixed to the rotary element. Contra-rotation of the flywheel may compensate for torque reaction forces when the rotary element is accelerated or decelerated.

20 Claims, 2 Drawing Sheets

TORQUE REACTION IN ROTATING MEDICAL APPARATUS

CROSS-REFERENCE TO RELATED PATENT APPLICATIONS

This application claims the benefit and priority of prior United Kingdom Patent Application No. 1606178.0, filed on Apr. 12, 2016, the entire contents of which are incorporated by reference herein.

FIELD OF THE INVENTION

The present invention relates to torque reaction in rotating medical apparatus, particularly but not exclusively oncology apparatus—"medical apparatus" is intended herein to encompass both radiotherapeutic apparatus and medical imaging apparatus which comprise systems which rotate around a patient.

BACKGROUND ART

Many designs of radiotherapy or radiation imaging apparatus employ a radiation source (such as a linear accelerator) mounted on a gantry arm that is rotatable around a patient support on which a patient can be placed for treatment, usually lying face upwards or supine. The usual geometry for this comprises a generally cylindrical, rotatable drum with a diameter of about 2 meters oriented in a vertical plane, i.e. with its axis of symmetry and rotation in a horizontal plane, with the gantry arm mounted onto the drum so that it projects outwardly from a circular face of the drum in cantilever fashion, offset from the axis of the drum. The radiation source is mounted at the end of the gantry arm distant from the drum, oriented so that the beam of radiation that it produces is directed towards the axis of rotation of the drum. The point at which the centre of the beam meets the axis is known as the "isocentre". In other designs there is no gantry arm, instead the radiation source is mounted to the cylindrical drum directly, usually towards its outer circumference. In all of these systems, as the drum rotates, the beam arrives at the isocentre from all angular directions within a vertical plane. This is an important aspect of radiotherapy treatment, as it allows a sufficient dose to be delivered to a target volume while minimising the dose delivered to surrounding healthy tissue, and it is important in rotary imaging, as it allows a very accurate image of a region of interest to be compiled from multiple images taken at many different angles.

Usually, the rotating drum is supported on a static support structure comprising four main wheels beneath the drum, arranged in two angularly-offset pairs, one pair at a front edge of the drum and one pair at a rear edge; alternatively there may be a pair of rollers extending between the front and rear edges of the drum. The drum and (where present) the gantry arm are usually very substantial items in order to support the weight of the radiation source mounted in the arm and at the end thereof—in modern radiotherapy systems the drum and gantry weigh between about 4 and 7 tonnes, and this weight is increased when the drum also supports another cantilever arm supporting further device, for example an imaging device (such as an EPID—Electronic Portal Imaging Device), opposite the radiation source for acquiring images of the patient from the attenuated radiation after it has passed through the patient's body. All forms of rotary drums, from a drum which has no gantry arm and is substantially cylindrical, to a drum which has one or more gantry arms supporting one or more devices are collectively referred to herein as "generally cylindrical rotary elements".

The rotation may be relatively constant in speed and/or direction, or it may "step" from one angular position to another, and/or it may change direction of rotation. The rotation speed is normally relatively slow, partly because the rotating parts are so massive and causing them to rotate and to stop or to change direction requires significant energy, and partly for reasons of health and safety. Health and safety also requires that the parts which are rotating in close vicinity to the patient can be brought quickly to a halt over a short angular distance, such as in an emergency; in order to stop a rotating body, a braking torque must be applied, and this torque must also be resisted by the supporting structure. There is a need to reduce the time taken for radiation imaging and treatment, so as to minimise the time each patient needs to spend inside the apparatus, and to allow more patients to be treated each day. One way of reducing treatment time would be to increase the rotational speed of the drum; however, stopping the rotation of a relatively massive device over a short angular distance exerts substantial reaction forces on the apparatus and the structure to which it is mounted; increasing the speed of rotation, and/or reducing the time for changes of rotational direction increases these forces to the extent that there is the possibility of slippage between the drum and the wheels, a need for multiple drive wheels to accelerate and decelerate the drum, and there are significant lateral loads to be borne by the base supporting structure for the drum. Dealing with these concerns necessitates extensive and expensive additions or modifications to be made to the apparatus, or in extreme circumstances it may not be practicable to address some or all of them and so the drum rotation speed would have to be reduced.

SUMMARY OF THE INVENTION

The present invention uses a contra-rotating flywheel which is driven coaxially relative to the rotary element of a medical apparatus for treatment or scanning/imaging of a patient; by "relative to" is meant that the flywheel is free to rotate and is accelerated and decelerated by means which are fixed to the rotary element, so that the reaction to the force driving the flywheel is provided by the rotary element. When accelerating the contra-rotating flywheel relative to the rotary element, a torque will develop between the rotary element and the contra-rotating flywheel, which will accelerate both in opposite directions. Once both elements are at speed, if the contra-rotating flywheel is decelerated, or braked, against the rotating rotary element to stop it or to reverse its direction of rotation, a braking torque will develop between both bodies, which will decelerate both in opposite directions, meaning that the external torque reaction forces exerted externally of the rotary element are significantly reduced. The rotary element may be generally cylindrical, or it may comprise a cantilevered arm having an end which carries a radiation source and which in use describes a circular path around the patient (known in the radiology field as a 'C-arm' apparatus).

The invention is primarily applicable to apparatus where the rotary element is significantly large and has a substantial mass—where it rotates about a diameter of more than about 1 m and/or is more than about 1 tonne in weight; however, the principles of the invention could also be applied to other, smaller medical or dental devices, such as drills or circular saws where torque reaction and/or gyroscopic forces arise, so the invention extends to the use of a contra-rotating flywheel driven relative to and coaxially with a rotary element of a medical treatment or imaging apparatus or of a dental apparatus, and the term "medical apparatus" used herein should be construed accordingly.

The present invention therefore provides a system for use with a medical treatment or imaging apparatus having a rotary element which, when the apparatus is in use, rotates about an axis, the system comprising a contra-rotating flywheel which is driven about the same axis and is driven relative to the rotating element, so that the flywheel is free to rotate and is accelerated and decelerated by means which are fixed to the rotary element.

Such an arrangement allows the rotary element to rotate at significantly higher speeds than in a conventional apparatus (so reducing the time for any treatment or imaging of the patient by a factor of at least 3), whilst significantly reducing torque reaction forces transmitted from the rotary element to the base support structure (which depend on the relative masses of the rotary element and the flywheel, their moments of inertia and their rotation speeds, as would be understood by the skilled person) and so reduce: skidding between the rotary element, or drum, and the wheels; having to have multiple wheels to drive/brake the drum, and lateral loads on the structure supporting the rotary element.

The flywheel may be located within the axial length of the rotary element, which is generally preferable when the patient being treated/imaged is located at least partially within the axial length of the rotary drum, or the flywheel may be located beyond the axial extremities of the rotary element. The flywheel may be larger in diameter than an internal diameter of the cylindrical rotary drum (preferable when the patient being treated/imaged is located at least partially within the axial length of the rotary drum), and it may be smaller than an external diameter of the drum, which provides for a diametrically compact arrangement (but which may have an adverse effect on the axial length of the drum); alternatively the flywheel may be larger in diameter than an external diameter of the cylindrical rotary drum, which would reduce the effect of the axial length of the drum but might have implications for the structure enclosing the rotary element. The flywheel need not be a flat disc, or even a rim with spokes, it could equally be in the form of an annulus, or any other suitable shape; it is a simple matter to modify the shape and configuration of the flywheel so as to "tune" the moment of inertia of the flywheel about its axis, given the moment of inertia of the rotary element and the planned angular velocities of the flywheel and drum, so as to optimise the torque reducing effects of the system. In applications where the patient is not located within the axial length of the drum, the flywheel could be rotatably mounted to an axial bearing; in other applications the flywheel could be supported by one or more circular bearings, on the inside and/or outside circumference(s) of the flywheel. The circular bearings could be in the form of roller bearings, of multiple rollers located around the circumference of the flywheel, or of any other suitable bearing arrangement. The bearing arrangement could be relative to the rotary element, or relative to the static base structure which supports the rotary element. Where the bearing arrangement is relative to the rotary element, the driver could be integrated in or alongside the bearing arrangement, with one of the rotary drum and the flywheel including the rotor and the other incorporating the stator. Additionally or alternatively there may be one or more electric motors fixedly disposed somewhere around the rotary element and connected in a suitable manner (e.g. a drive roller, drive band or the like) so as to drive the flywheel to contra-rotate relative to the rotary element.

The flywheel may be of smaller mass than the rotary element. Whilst the moment of inertia of the flywheel will depend on its shape and configuration, we prefer to "match" the moment of inertia of the flywheel to that of the rotary element so that the flywheel can rotate faster than the rotary element. This permits a less massive flywheel to oppose torque reaction effects arising from the acceleration/deceleration of a more massive rotary element.

The system may also comprise additional means for decelerating the flywheel relative to the rotary drum, such as disc or drum type brakes. Additional brakes would enable the rapid deceleration of the rotary element, over a small angle, when this may be necessary, such as in an emergency.

The invention also provides a method of compensating for torque reaction forces in a medical apparatus comprising a rotary element which, in use rotates around an axis, the method comprising driving a contra-rotating flywheel relative to the rotary element, so as to rotate coaxially with the rotary element and in the opposite direction, and so that the flywheel is free to rotate and is accelerated and decelerated by means which are fixed to the rotary element. The flywheel may be driven at a higher angular velocity than the rotary element, with their respective moments of inertia being matched as appropriate. Such arrangements allow a massive rotating oncology apparatus to be operated at a significantly higher speed

BRIEF DESCRIPTION OF THE DRAWINGS

The invention will now be described by way of example and with reference to the accompanying figures, in which.

DETAILED DESCRIPTION OF THE EMBODIMENTS

Figure 1:
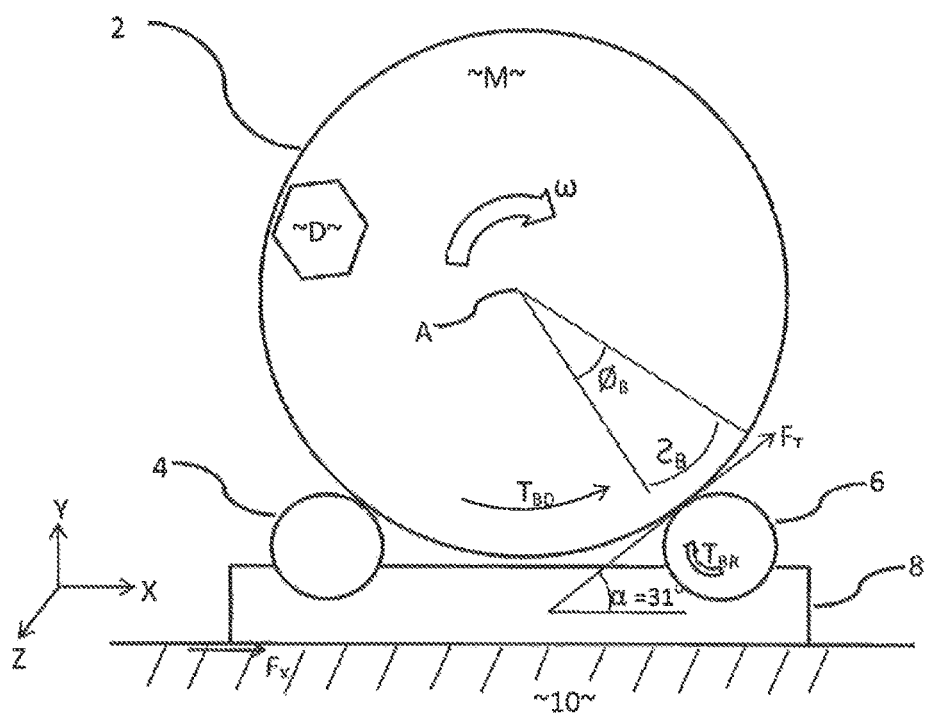
FIG. 1 is a schematic diagram of a typical oncology system which is configured to rotate around a patient.
Figure 2:
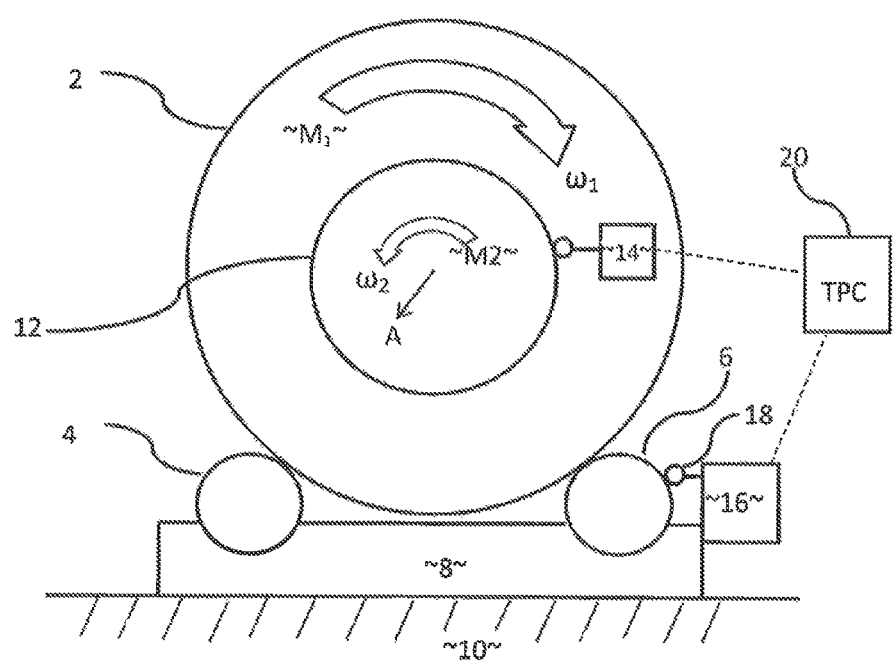
FIG. 2 is a schematic diagram, similar to that of FIG. 1, but illustrating in principle how the present invention might be implemented.

FIG. 1 shows in schematic form a radiotherapy or radiation imaging apparatus comprising a generally cylindrical drum 2 which is arranged to rotate about an axis A parallel to the Z axis, along which a patient (not shown) may be positioned for treatment/imaging, and along which the isocentre lies. In many apparatuses which would be suitable for the system of this invention, the patient is supported on a support which is movable with multiple degrees of freedom (at least along the three orthogonal X, Y and Z axes, and often also around one or more of these axes); the patient is introduced inside the cylindrical drum generally along the Z axis and his/her orientation within the drum is adjusted so as to ensure the region of interest (such as a tumour) is located accurately relative to the isocentre by movements along and/or around the three axes The drum 2 is supported on wheels 4, 6 disposed to left and right of the drum along the X axis as shown; one or more of these wheels is driven so as to cause the drum 2 to rotate (a motor 16 for this purpose is shown in FIG. 2). The wheels 4, 6 are part of a base support 8 which is secured to the floor 10. Mounted to the drum 2 towards its outer circumference (sometimes on a gantry arm extending in the Z direction, and other times mounted to the axial edge or internal circumference of the cylindrical drum) is a treatment or imaging device D, which is configured to emit therapeutic or imaging radiation or energy towards the axis A (and a region of interest of the patient located (but not shown) there); there may be more than one such device D located at different angular positions around the circumference of the drum 2, and there may be imaging devices (not shown) arranged on the circumference of the drum opposite the or each device.

The drum 2 and device(s) D have a substantial mass M—in the case of a typical radiotherapy apparatus comprising a linear accelerator, this is in the order of 4 to 7 tonnes—and, in use rotates in the direction shown by the large curved arrow with an angular velocity ω. It is well known that:

$$E_C = \tfrac{1}{2} I_C \omega^2 \tag{1}$$

where $E_C$ is the kinetic energy stored in the rotating drum and gantry and $I_C$ is the moment of inertia of the drum and gantry around the axis of rotation A.

It is also known that:

$$T_{BD} = E_C / \varnothing_B \tag{2}$$

where $T_{BD}$ is the braking torque required to halt the rotation of the drum and gantry within an angle $\varnothing_B$, $$F_T = T_{BD}/R \tag{3}$$

where $F_{BD}$ is the tangential force required at radius R from the axis A to stop the rotation of the drum within an angle $\varnothing_B$, and $$F_X = F_T \cos \alpha \tag{4}$$

where $F_X$ is the force exerted on the floor by the base support during braking of the drum's rotation when this is carried out by the wheel 6. It will be appreciated that $F_T$, the tangential braking force is limited by the coefficient of friction between the drum 2 and the wheel 6. In a conventional apparatus the drum typically rotates at around 1 rpm: this means that the tangential braking force $F_T$ is in the order of 8 kN and the force exerted on the floor $F_X$ is in the order of 7 kN. It can be appreciated that forces of these magnitudes are sufficient to risk undesirable slippage of the drum 2 on the wheels 4, 6, and also damage to whatever means is used to retain the base support 8 in position on the floor 10, and/or movement of the base support 8 across the floor. To increasing the rotational speed of the drum would significantly increase these risks.

EXAMPLE

A typical radiotherapy apparatus comprising a linear accelerator (~6 tons) rotating at 1 RPM has a kinetic energy of ~33 J. At 3 RPM the stored energy increases to ~300 J as energy is proportional to the square of speed. The stopping distance is dependent on the reaction time of the system and the braking torque that can be applied. In the type of apparatus where (as shown in the figures) the drum is mounted on the wheels by gravity alone the braking torque is effected through wheel/rim contact. Assuming a stopping distance of 3 degrees, a rotational speed of 3 RPM and 60 ms reaction time, the drum will rotate 1 degree before actively braking over the next 2 degrees.

To oppose the rotation (brake) at 1 m distance from the centre (drum/wheel interface) a force must be applied as follows:

$$E = F_B * (R * \theta) = 300 \text{ J}$$

$$F_B = 350 \text{J}/(1 \text{ m} * (2\pi/360°) * 2) = 8.6 \text{ kN}$$

The typical force between the drum and the support wheels (such as in the case of the linear accelerator sold by Elekta AB (publ) under its Versa HD trade mark) is ~17.5 kN which means that, assuming dry friction between the steel drum and the steel roller wheels gives a maximum braking force of $$F_T = 8600 * 0.2 = 3.5 \text{ kN per wheel}$$

the stopping torque must be transmitted via at least 3 wheels to avoid slippage between the wheels 4, 6 and the drum.

The tangential force between the wheel(s) and the drum 2 will also lead to a sideways force on the base structure 8 and thence to the floor 10 as follows:

$$F_X = F_B \cos(\alpha) = 8{,}600 * \cos 31 = 73 \text{ kN}$$

FIG. 2 demonstrates the principle of the present invention. The drum 2 of mass $M_1$ rotates at angular velocity $\omega_1$; it is driven by motor 16, which acts through drive element 18 to turn wheel 6 on which drum 2 rests. A flywheel 12 of mass $M_2$ rotates at angular velocity $\omega_2$; about the same axis A as the drum 2, but in the opposite direction as shown by the smaller curved arrow. Flywheel 12 is driven to rotate by motor 14, which is fixedly mounted to the drum 2, and which can also be used for braking the rotation of the flywheel. Because the flywheel contra-rotates relative to the drum, on starting the drum 2 and flywheel 12 rotating, the acceleration of the flywheel 12 imparts a torque on the drum in the opposite direction to the rotation of the flywheel and causes the drum to rotate in the opposite direction. Assuming for the moment that there are no losses due to friction, then the kinetic energy of the rotating flywheel $E_2$ will equal the kinetic energy of the rotating drum $E_1$ at any time, and the relative absolute speeds will be related to the respective moment of inertia:

$$\omega_1^2/\omega_2^2 I_2/I_1. \tag{5}$$

Because $E_1 = E_2$ at any time, when braking, or decelerating the flywheel 12, the resulting torque between the flywheel 12 and the drum 2 will result in both flywheel and drum stopping within the same stopping angle.

In practice there are frictional losses, hence embodiments of the invention require something to accelerate and decelerate rotation of the flywheel 12 relative to the drum 2, such as motor 14, and also something to drive drum 2 to compensate for frictional losses, such as motor 16, which drives drum 2 (indirectly as shown, or directly) relative to the floor 10.

The use of a contra-rotating flywheel 12 which is driven relative to the drum 2 in the way described significantly reduces the external reaction forces arising from when the drum 2 is accelerated and, more significantly, when it has to be decelerated quickly and/or within a small angle of rotation of the drum, because a large proportion of what the total external forces would be (i.e. absent the flywheel) are absorbed in the acceleration/deceleration of the rotation of the flywheel. Because it is very important to be able to stop the drum 2 rotating quickly and to cope with the torque reactions arising from this, additional means may be provided to brake the flywheel 12, such as conventional brake pads fixed relative to the drum and acting on the flywheel (or fixed relative to the flywheel and acting on the drum); the braking system may be of a conventional drum and/or disc type, with the flywheel or drum being provided or configured with a suitable braking surface. In this case, the motors would be augmented by the brakes, meaning that the motors are subject to less braking wear. We envisage that the contra-rotating flywheel 12 would be of lower mass than the drum 2, but rotates at a higher speed than the drum (as an example, a flywheel comprising a 50 kg disc with a 1 m diameter rotating at 66 RPM will contain the same energy as a 6 tonne drum rotating at 3 RPM). On braking, the energy will be lost as heat in the brakes and/or in the drive motors (to the extent these are used). Due to friction in the system, there will need to be an external drive as well as an internal drive. Furthermore, as two separate bodies are accelerated in absolute terms, twice the energy is required to accelerate a system in accordance with the invention than in a conventional apparatus.

The apparatus is controlled by a processor 20 (in the case of a radiotherapy apparatus this is usually known as a Treatment Planning Computer, or "TPC"); in FIG. 2, the processor 20 is shown operatively connected to the two drive motors 14, 16, but for clarity the other connections, such as to the device D shown in FIG. 1, are not shown in FIG. 2.

It will of course be understood that many variations may be made to the above-described embodiment without departing from the scope of the present invention. For example, although described as a flywheel, provided that the contra-rotating element has an appropriate mass and moment of inertia it could be of any shape and configuration provided it had rotational symmetry: a contra-rotating annulus might be more suitable in applications where the drum is hollow for receiving a patient, for example, whereas a more conventional flywheel might be appropriate where the drum is closed and the gantry alone rotates around the patient. The contra-rotating element or flywheel might be confined within the axial length of the drum, or it might be outside the axial length of the drum. It may be advantageous in some applications to have two, three or more smaller contra-rotating coaxial flywheels rather than a single larger flywheel. The drive elements 18 may be driven rollers which bear on the wheels or the flywheel, gears, or any other suitable driving connection. The drive motors 14, 16 can be electric motors as described, or hydraulic motors. The rotary element may be a generally cylindrical element, as shown, or it may be any other type of rotary element, such as a C-arm. Where different variations or alternative arrangements are described above, it should be understood that embodiments of the invention may incorporate such variations and/or alternatives in any suitable combination.

As explained above, the present invention is applicable to any form of oncology apparatus which has a significant element of substantial size and/or mass which in use is required to rotate around a patient; thus, the invention may be implemented on a radiotherapeutic apparatus having a radiation source such as a linear accelerator (such as is described in our EP2399647), a magnetic resonance imaging linear accelerator ("MLR"—(such as is described in our EP2865419) or an isotopic source, or it may be implemented on any form of tomographic scanning or rotary imaging apparatus (whether this is used for oncological or other medical purposes) such as CT (Computed Tomography), PET (Positron Emission Tomography), SPEC (Single-Photon Emission Computed Tomography), EPID or ultrasound scanners.

The invention claimed is:

1. A system for use with a medical apparatus having a rotary element which rotates about an axis, the system comprising:
    a contra-rotating flywheel which is driven to rotate about the axis relative to the rotary element, wherein the flywheel is free to rotate and is accelerated and decelerated by a driver which is fixed to the rotary element.

2. The system according to claim 1, wherein the flywheel is located within an axial length of the rotary element.

3. The system according to claim 1, wherein the rotary element is cylindrical.

4. TL system according to claim 3, wherein the flywheel has an outer circumference larger in diameter than an internal diameter of the cylindrical rotary element.

5. The system according to claim 4, wherein the outer circumference of the flywheel is smaller than an external diameter of the cylindrical rotary element.

6. The system according to claim 1, wherein the rotary element is a C-arm apparatus.

7. The system according to claim 1, further comprising one or more motors for driving the flywheel relative to the rotary element.

8. The system according to claim 1, wherein the flywheel comprises a rotor of an electric motor and the rotary element comprises a stator of the electric motor.

9. The system according to claim 1, further comprising one or more brakes configured to selectively decelerate the rotation of the flywheel relative to the rotary element.

10. The system according to claim 1, wherein the flywheel has a mass and/or a moment of inertia less than that of the rotary element.

11. The system according to claim 1, further comprising a processor for controlling the rotation of the rotary element and the contra-rotation of the flywheel.

12. A method of compensating for torque reaction forces in a medical apparatus comprising a rotary element which rotates around an axis, the method comprising:
    driving a contra-rotating flywheel relative to the rotary element, wherein the flywheel rotates around the axis in the opposite direction of the rotary element, and wherein the flywheel is free to rotate and is accelerated and decelerated by a driver which is fixed to the rotary element.

13. The method according to claim 12, wherein the flywheel is driven to rotate at a different angular velocity than the rotary element.

14. The method according to claim 13, wherein the flywheel is driven to rotate at a higher angular velocity than the rotary element.

15. The system according to claim 1, wherein the medical apparatus is one of a medical treatment apparatus, an imaging apparatus, or a dental apparatus.

16. The system according to claim 1, wherein the rotary element is a hollow drum configured for receiving a patient therein.

17. The system according to claim 16, wherein the flywheel is annular.

18. The system according to claim 1, wherein the rotary element is a closed drum configured for rotating a gantry arm about a patient.

19. The system according to claim 18, wherein the gantry arm has a treatment or imaging device mounted thereon.

20. The system according to claim 1, wherein a treatment or imaging device is mounted upon an internal circumference of the rotary element.

* * * * *

UNITED STATES PATENT AND TRADEMARK OFFICE
CERTIFICATE OF CORRECTION

PATENT NO. : 10,371,232 B2  
APPLICATION NO. : 15/484336  
DATED : August 6, 2019  
INVENTOR(S) : Per Harald Bergfjord Page 1 of 1

It is certified that error appears in the above-identified patent and that said Letters Patent is hereby corrected as shown below:

Claim 4, Column 8, Line 7:  
"TL system" should read --The system--.

Claim 10, Column 8, Line 25:  
"has a mass and/or a moment" should read --has a mass or a moment--.

Signed and Sealed this  
Seventeenth Day of September, 2019

Andrei Iancu  
*Director of the United States Patent and Trademark Office*

UNITED STATES PATENT AND TRADEMARK OFFICE
CERTIFICATE OF CORRECTION

Page 1 of 1

PATENT NO. : 10,371,232 B2
APPLICATION NO. : 15/484336
DATED : August 6, 2019
INVENTOR(S) : Per Harald Bergfjord It is certified that error appears in the above-identified patent and that said Letters Patent is hereby corrected as shown below:

On the Title Page

Below item (58), Insert the following:
--(30) Foreign Application Priority Data
April 12, 2016  (UK) . . . . . . . . . . . . 1606178.0--

Signed and Sealed this
Seventeenth Day of March, 2020

Andrei Iancu
*Director of the United States Patent and Trademark Office*